United States Patent [19]

Bissonette

[11] Patent Number: 4,725,277

[45] Date of Patent: Feb. 16, 1988

[54] INTRAOCULAR LENS WITH TAPERED HAPTICS

[75] Inventor: Noel G. Bissonette, Richfield, Minn.

[73] Assignee: Precision-Cosmet Co., Inc., Minneapolis, Minn.

[21] Appl. No.: 862,989

[22] Filed: May 14, 1986

[51] Int. Cl.⁴ .......... A61F 2/16

[52] U.S. Cl. .......... 623/6

[58] Field of Search .......... 623/6

[56] References Cited

U.S. PATENT DOCUMENTS

| | | | |
|---|---|---|---|
| Re. 31,626 | 7/1984 | Hoffer | 623/6 |
| 4,159,546 | 7/1979 | Shearing | 623/6 |
| 4,174,543 | 11/1979 | Kelman | 623/6 |
| 4,370,760 | 2/1983 | Kelman | 623/6 |
| 4,435,855 | 3/1984 | Pannu | 623/6 |
| 4,468,820 | 9/1984 | Uhler et al. | 623/6 |
| 4,476,591 | 10/1984 | Arnott | 623/6 |
| 4,477,931 | 10/1984 | Kelman | 623/6 |
| 4,494,254 | 1/1985 | Lopez | 623/6 |
| 4,556,998 | 12/1985 | Siepser | 623/6 |

FOREIGN PATENT DOCUMENTS

| | | | |
|---|---|---|---|
| WO85/00965 | 3/1985 | PCT Int'l Appl. | 623/6 |

OTHER PUBLICATIONS

Ocular Surgery News (Reprint), Sep. 1, 1984, vol. 2, No. 17.

"Experience with Twelve Cases of Intra-Ocular Anterior Chamber Implants for Aphakia", by J. Bober-g-Ans, British Journal of Ophthalmology, vol. 45, No. 1 Jan. 1961, pp. 37–43.

Precision-Cosmet Product Information Sheets, 1985.

Implantation Procedure for the Bechert 7 mm One--Piece Posterior Chamber Lens, by Charles H. Bechert, M.D., 5 pages.

Implantation of the Kratz/Johnson 7.0 mm Posterior Chamber Lens, by Richard P. Kratz, Stephen H. Johnson, M.D., 5 pages, 1985.

Implant Techniques, The Kamerling Capsular 90 PCL, by William Kamerling, 4 pages.

*Primary Examiner*—Ronald L. Frinks

*Attorney, Agent, or Firm*—Merchant, Gould, Smith, Edell, Welter & Schmidt

[57] ABSTRACT

An intraocular lens for use as an artificial lens implant is disclosed. The intraocular lens includes an optical lens body having a periphery and two curved, elongated and resilient haptic members for positioning and supporting the lens in the eye. Each haptic member has an inner or root end and an outer or free end. The haptic member are integrally formed with the lens body as a one-piece construction at the root ends thereof. The haptic members extend outwardly from the lens body along an arc exterior to the periphery of the lens body. Each haptic member has at least a portion thereof tapered or reduced in cross sectional dimension in a direction therealong from the root end toward the free end.

10 Claims, 11 Drawing Figures

10 26a 24a 22b 5 14 20a 12c 16 15a 20b 14 15 13 12 12a 22a 24b 26b 12d 5

10
26a
24a
22b
5
14
20a
12c
16
15a
20b
14
15
13
12
12a
22a
12d
24b
26b
5

10
12
12a
14
15a
16
12c
24a
26a
h'
20b
24b
26b
17
22b
12b
12d
24
22a
15
13
20a 7
6
26b
24b
20b
22b
7
6

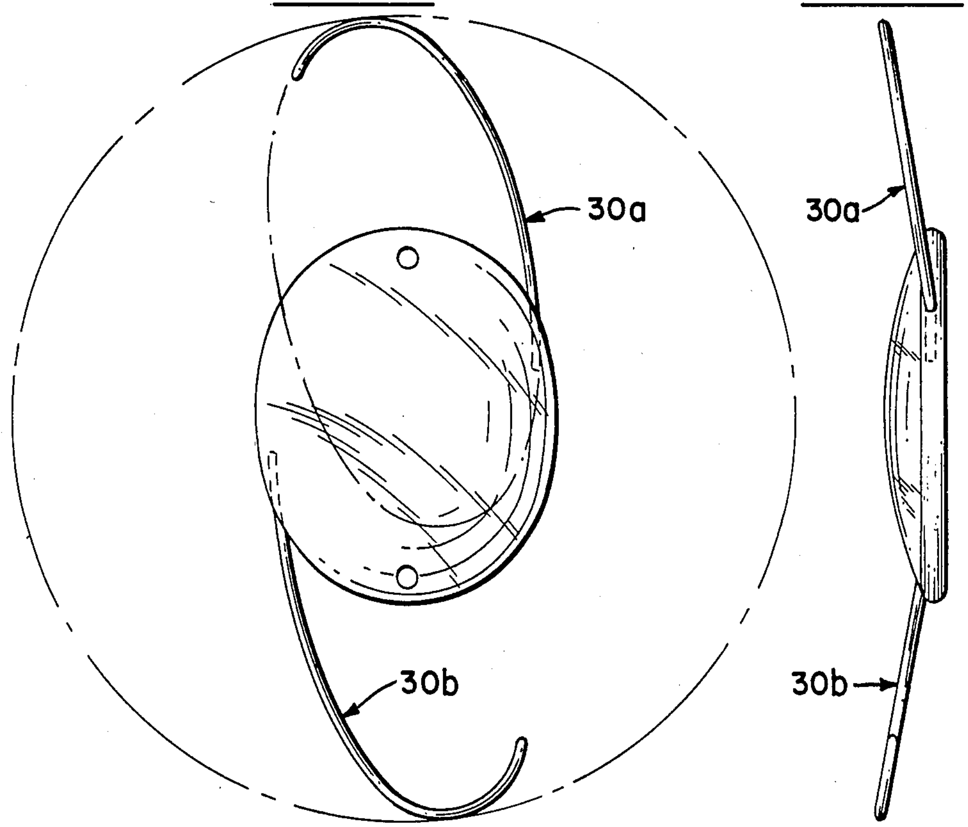
FIG. 3
PRIOR ART
30a
30b
FIG. 4
PRIOR ART
30a
30b
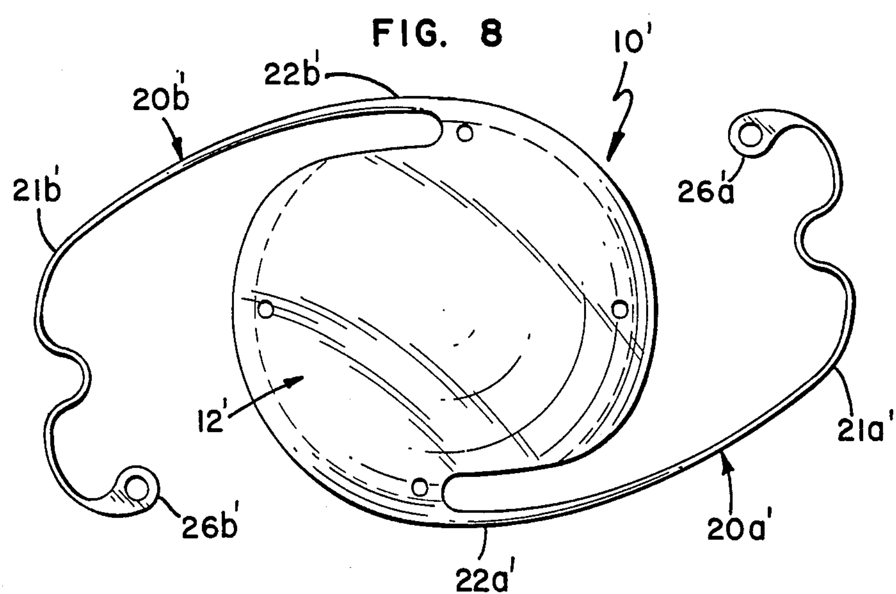
FIG. 8
10'
22b'
20b'
21b'
26a'
12'
21a'
26b'
20a'
22a'

20a''
10''
12''
20b''

20b
24a 20b
22b 48
50
24a
20a
46b
42
15
14
13
17
44
46a
15a
10
46
22a
24
12b
16
12
12d
12a
26b
12c
17
14
24b
46c
20b
50
40

48
42
50
20a"
46b
40
44
12"
10"
46a
24
46
44
20b"
50

INTRAOCULAR LENS WITH TAPERED HAPTICS

TECHNICAL FIELD

This invention relates generally to intraocular lenses to be used as artificial lens implants in eyes from which the cataractous natural lens has been removed, and more particularly to an improved structure for the haptic elements of an intraocular lens.

BACKGROUND

The implantation of an intraocular lens for restoring vision after cataract surgery is well-known in the art. In general, two forms of surgery are used to remove cataracts. These are extracapsular cataract extraction and intracapsular extraction. (Discussed in U.S. Pat. Re. No. 31,626 to Hoffer). Following extraction of a cataractous lens, an intraocular lens is normally implanted in either the anterior or the posterior chamber of the eye. In an anterior chamber implant, the lens is generally situated forward of, or mounted to the iris. In the case of posterior chamber implants, the lens is situated behind the iris and may be mounted within the cleft or fornix of the capsule which remains in place after extracapsular surgery.

In both anterior or posterior chamber implants, the lens is usually centered and fixed in position by one or more supporting strands or haptic members. While available intraocular lenses incorporate haptic member(s) having various geometric shapes and configurations, the typical haptic member is a flexible strand of non-biodegradable material which is fixed to the lens body, and exhibits specific spring-like memory qualities so that the haptic member can be compressed or off set from the normal rest position and thereafter returned to the fully extended condition when pressure is removed. (See U.S. Pat. Nos. 4,468,820 to Uhler et al.; 4,435,855 to Pannu; and 4,494,254 to Lopez.)

The typical diameter or thickness of a haptic member is about 0.1–0.2 mm; and therefore requires careful handling prior to and during implantation of the lens. For example, a haptic member can break or weaken when improperly handled with a surgical instrument, such as forceps. A broken haptic renders the lens useless. In the case of an integral one-piece lens a broken haptic requires that an entirely new lens be used.

While not common, it is possible that improper handling of a haptic prior to lens implantation may damage the haptic without breaking it. If a lens with a damaged haptic is implanted and the haptic breaks subsequent to surgery, serious complications can arise. Dislocation of a lens subsequent to surgery could seriously impair vision and/or damage the eye.

Among the wide variety of intraocular lenses having haptic support members, all known haptics have a uniform cross sectional dimension or thickness. When pressure is applied to the haptic (i.e. grasping root or base area of haptic with forceps) stress is concentrated at a relatively small area, thereby increasing the potential for breakage in the area of concentrated stress.

It is well known that distortion of the eyeball can be caused by normal physical activities such as walking or rubbing the eyelids, as well as by more severe physical contact such as falls or collisions. When an intraocular lens has been implanted, distortion of the eyeball can place intermittent stress on the haptic members. This intermittent stress generally results in eye irritation, redness or other minor trauma. It is believed that these intermittent stresses can be minimized by increasing the flexibility of the haptic members. However, if haptics of the type currently available are made thinner to increase flexibility, the potential for breakage is also increased.

Accordingly, a substantial need exists for a haptic support member which exhibits high resistance to breakage when handled. The present invention provides an artificial lens having an improved haptic member which is strengthened to minimize breakage. The strengthened haptic member of the present invention also provides for thinner more flexible haptics without sacrificing needed strength.

SUMMARY OF INVENTION

The present invention is an intraocular lens for use as an artificial lens implant in an eye. The intraocular lens has an optical lens body and an improved means for positioning and supporting the lens body in the eye. Particularly, the lens body of the present invention is positioned and supported in the eye by at least one resilient haptic member having a root end and a free end. The haptic member is connected to the periphery of the lens body at the root end thereof. Preferably, the haptic member and lens body are integrally formed as a one-piece construction at the root end. The haptic member extends outwardly from the lens body along an arc exterior to the periphery of the lens body and is strengthened by having at least a portion thereof tapered in a direction along its length from the root end toward the tip. The tapered portion of the haptic member distributes externally applied stresses over a substantial length of the haptic member, thereby avoiding concentration of stress and minimizing the potential for breakage in the area of concentrated stress.

In a preferred embodiment of the present invention, two curved elongated and resilient haptic members are integrally formed with the lens body at the periphery thereof. The two haptic members extend tangentially therefrom along an arc exterior to the periphery and have a cross sectional dimension which is reduced over at least a portion thereof in a direction along the length of the haptic from the root end toward the free end.

In one embodiment of the present invention, the haptic members have a circular cross section which is reduced along all dimensions of the haptic in a direction along the entire length from the root end to the tip of the free end. In an alternate embodiment, the haptic members have a circular cross section which is reduced only over a portion of each haptic in the direction therealong from the root end toward the free end.

In all preferred embodiments, the haptic members or members are tapered proximate the root end in the direction from the root end toward the free end. Inclusion of a tapered portion in at least the area of the root end increases the haptic's resistance to fracturing without compromising flexibility.

The present invention makes possible thinner, more flexible haptics which can withstand greater deformation without fracturing. More flexible haptics such as provided for by the tapered haptics of the present invention can: adapt to distortion of the eye resulting from activities such as rubbing and pressing; deflect independently; adapt to the shape of the eye to equalize pressure; uniformly deflect in a plane perpendicular to the plane of the optic of the lens; control deflection forces over a broad area of the eye; and reduce tenderness in the eye. Accordingly, the advantages of increased flexibility made possible by the present invention provide for a safer, more comfortable and better performing intraocular lens.

These and various other advantages and features of the novelty which characterizes the invention are pointed out with particularity in the claims annexed hereto and forming a part hereof. However, for better understanding the invention, its advantages, and objects attained by its use, reference should be had to the drawings which form a further part hereof and to the accompanying descriptive matter in which there is illustrated and described a preferred embodiment of the invention.

BRIEF DESCRIPTION OF THE DRAWING

FIG. 3 is a top plan view of a prior art intraocular lens.

FIG. 4 is a side elevational view of the prior art lens shown in FIG. 3.

FIG. 8 is a top plan view of an alternate embodiment of the intraocular lens of the present invention.

DETAILED DESCRIPTION OF THE INVENTION

Figure 1:
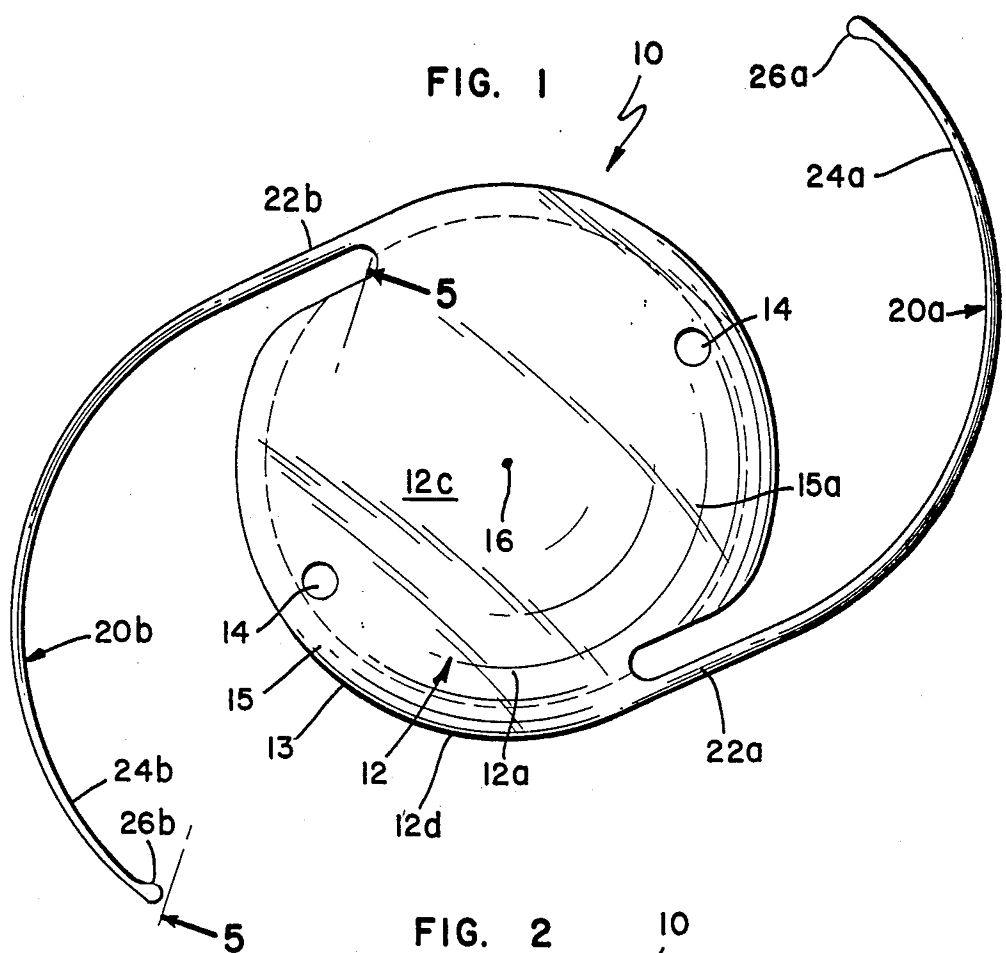
FIG. 1 is a top plan view of a preferred embodiment of the intraocular lens of the present invention.

Referring to the drawings, wherein like numerals represent like parts throughout the several views, an intraocular lens designated generally as 10 incorporating the present invention is shown in FIGS. 1, 2 and 5–7.

Figure 2:
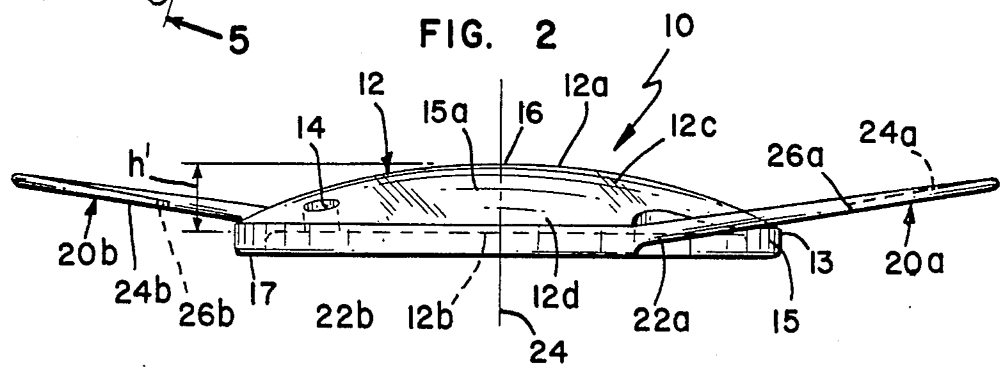
FIG. 2 is a side elevational view of the lens shown in FIG. 1.

The intraocular lens 10 includes a central optical region or lens body 12 which preferrably, although not necessarily, is of a plano-convex cross-section. As shown in FIGS. 1 and 2, the optical lens body 12 has an upper portion 12*c* with an anteriorly convex upper surface 12*a* and a base portion 12*d* with a posteriorly substantially planer bottom surface 12*b*. The base portion 12*d* is relatively thin compared to the upper portion 12*c*. The optical lens body 12 has an apex 16, and a peripheral zone 15 including the outer periphery or circumference 13 of the lens body 12. The peripheral zone 15 is exterior to the optical zone 15*a* of the lens. The lens body 12 has a height h' as shown in FIG. 2, of a distance between the apex 16 and the bottom surface 12*b*. The height h' can be characterized as the distance from the apex 16 to the bottom surface 12*b* measured along the optical axis 24 of lens body 12. Interconnected to the periphery 13 of the lens body 12 are two curved elongated haptic members 20*a,b* extending outwardly from the lens body 12 along an arc exterior to the periphery 13. While the haptic members 20*a,b* as shown in FIG. 1, extend from the periphery 13 it is to be understood that the haptic members could extend outwardly from points anywhere within the peripheral zone 15.

The lens body 12 of the lens 10 is centered and retained within the eye by the flexible haptic members 20*a,b*. As shown in FIG. 1, the haptic members 20*a,b* include root ends 22*a,b* connected to the periphery 13 of the lens body 12 and outer or free ends 24*a,b* which each terminate at a tip 26*a,b*. In the preferred embodiment shown in FIG. 1 the cross sectional dimension or diameter of the tip 26*a,b* is slightly enlarged to minimize irritation to the eye. Particularly, the curved haptics with rounded ends fit snugly but comfortably inside the eye but avoid single point pressure which can lead to undesired complications, such as zonule rupture or ciliary body pressure in posterior chamber implants.

In the preferred embodiment shown in FIG. 1, the haptic members 20*a,b* are spaced and located approximately across the diameter of the lens body 12. While the haptic members 20*a,b* may be connected to the lens body 12 at the periphery 13 thereof by a number of known methods, in the preferred embodiment shown, the haptic members 20*a,b* and the lens body 12 are formed as an integral one-piece structure by forging and machining process. However, it will be appreciated that the lens 10 may also be produced by other suitable methods such as injection molding and lathing.

In the preferred embodiment of FIGS. 1 and 2 the arc traversed by the haptic members 20*a,b* is substantially circular and curved toward the periphery 13 of the lens body 12. It is to be appreciated that arcuate shaped haptics of a wide variety of shapes and designs are known such as "J" shaped (U.S. Pat. Nos. 4,468,820 to Uhler et al; 4,435,855 to Pannu) and "C" shaped (U.S. Pat. Nos. 4,477,931 to Kelman; 4,494,254 to Lopez). The lens of the present invention could incorporate haptics with any of these known shapes and designs, including a single haptic member or a combination of a single flexible haptic member together with an inflexible haptic support element.

The haptic members 20*a,b* are easily compressed and held in a deformed condition thereby facilitating insertion of the lens into the eye. Particularly, the resilient haptic member members 20*a,b* spontaneously tend to return to a normal position when released after being forced into the deformed position. This provides an intraocular lens which when positioned in the eye is self-fixating and self-centering and displays less of a tendency to tilt after being implanted in the eye.

The intraocular lens body 12 is made of a biologically tolerable and optically suitable material such as polymethylmethacrylate (PMMA). The haptic members 20*a,b* are made of a flexible, compressible, resilient plastic material such as PMMA or polypropylene. Preferably, the entire lens 10 is made as an integral one-piece structure of PMMA.

A prior art lens, including haptic members 30*a,b* with the known uniform cross sectional dimension is shown in FIGS. 3 and 4. In contrast to the known structure for haptic members, according to the present invention the lens 10 is provided with haptic members 20*a,b* having at least a portion thereof tapered (i.e. reduced in cross sectional dimension) in the direction along the length from the root ends 22*a,b* toward the free ends 24*a,b*.

Figure 5:
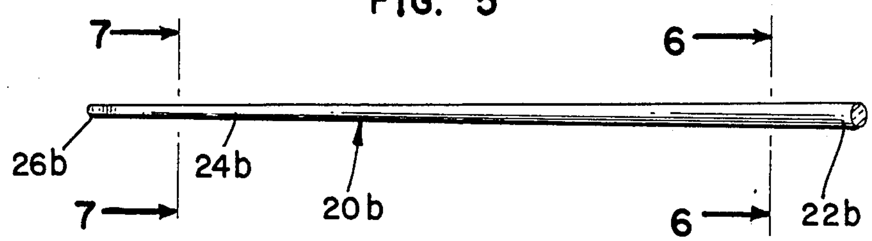
FIG. 5 is an elevational view taken along the line 5—5 in FIG. 1 showing one embodiment of the taper of the haptic member of the present invention.
Figure 7:
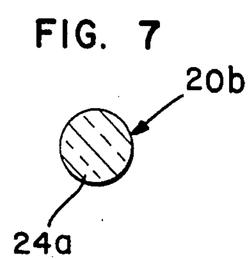
FIG. 7 is a sectional view taken along line line 7—7 in FIG. 5.
Figure 6:
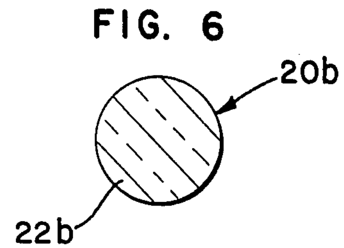
FIG. 6 is a sectional view taken along line 6—6 in FIG. 5.

The preferred embodiment shown in FIGS. 1 and 2 includes fiber like haptic members 20*a,b* tapered along all dimensions of the length from the root ends 22*a,b* to the rounded tips 26*a,b* of the free ends 24*a,b*. More particularly, each of the haptic members 20*a,b* extends tangentially from the periphery 13 along a substantially circular arc exterior to the periphery 13. Each haptic 20*a* and 20*b* traverses an arc of about 140°. Each haptic member 20*a* and 20*b* has a circular cross section which is reduced along all dimensions of the haptic fiber, as best shown in FIGS. 5-7. While the preferred embodiment shown in FIGS. 1, 2 and 5-7 includes haptics having a circular cross section, other geometric shapes can be employed by one skilled in the art. By way of example only the cross sectional dimension for the tapered haptic can be rectangular, square or oval.

It is to be understood that while the preferred embodiment in FIGS. 1 and 2 shows haptic members tapered from the root ends 22*a,b* toward the free ends 24*a,b* over substantially the entire length of the haptics 20*a,b* the haptic members need only be tapered over a portion thereof in a direction along the length from the root ends 22*a,b* toward the free ends 24*a,b* in order to increase resistance to fracturing. The cross sectional dimension of a partially tapered haptic will be smaller at the free end than at the root end or base.

An alternate embodiment 10' is shown in FIG. 8 in which only a portion of the haptic members 20*a',b'* is tapered along the length from the root ends 22*a',b'* in the direction of the tips 26*a',b'*. In FIG. 8, the taper or area of reducing cross section of the haptic members 20*a',b'* extends only from root ends 22*a',b'* to outer points 21*a',b'* along the length of the haptic members. While extending the area of taper over a greater portion of the haptic increases flexibility, it is to be understood that in order to significantly strengthen the resistance of the haptic member to breakage, only the portion of the haptic substantially adjacent or proximate the root ends 22*a,b* need be tapered.

In another alternate embodiment not shown, substantially rectangular haptic members having one surface facing the periphery of the lens body and an opposite surface facing away from the periphery may be tapered by reducing the distance between the periphery facing and periphery opposing surfaces over at least a portion of each haptic member along the length from the root end toward the free end.

Providing an intraocular lens with the tapered haptic of the present invention provides for a more even distribution of stress over the length of the haptic member than is exhibited by a haptic member having a uniform cross sectional dimension along its entire length as seen in FIGS. 3 and 4. An intraocular lens with a tapered haptic member also makes possible thinner more flexible haptics without compromising stength. By way of example, a typical haptic such as seen in FIGS. 3 and 4 has a diameter between 0.01 and 0.02 mm. over the entire length of the fiber. In contrast to this, haptics 20*a,b* such as seen in FIG. 1 can be tapered from 0.15 to 0.08 mm in the direction from the root ends 22*a,b* toward the free ends 24*a,b*. The thinner tapered haptic not only exhibits greater flexibility but also possesses greater resistance to fracture. More flexible haptics in accordance with the present invention will ease handling of the lens prior to and during positioning in the eye and provide for more comfortable and better performing lens.

The present invention is applicable to intraocular lenses 10 of all geometric shapes and configurations. Intraocular lenses 10 including the tapered haptics 20*a,b* of the present invention can be adopted for use as both posterior chamber intraocular lens implants as seen in FIG. 10 as well as anterior chamber intraocular lens implants as seen in FIG. 11.

The preferred embodiment of the lens 10 shown in FIG. 1 is of the type designed for posterior chamber implantation and includes an annular lip 17 projecting only rearwardly from the bottom surface 12*b*. When the lens 10 is implanted in the posterior chamber 42 as seen in FIG. 10 the annular lip 17 sits against the posterior capsule 46 and creates a space between the capsule 46 and rear of the optical zone 15*a* of the lens body 12. The preferred embodiment shown in FIG. 1 also includes positioning holes 14.

The posterior chamber type lens 10 will typically be utilized following extracapsular cataract extraction. As illustrated in FIG. 10, the lens 10 is implanted in a human eye 40, in the posterior chamber 42 behind the iris 44. Preferably, the cataract has been extracted from the capsular bag 46, leaving intact the posterior wall 46*a* and an annular flap portion 46*b* forming a cleft or fornix 46*c*. The capsular bag 46 is connected to the ciliary muscle in the eye wall 48 via suspensory ligaments 50. Vitreous humor in the region 52 behind the capsular bag 46 is prevented from flowing forward by the posterior wall 46*a* which assumes a generally planar shape.

Figure 10:
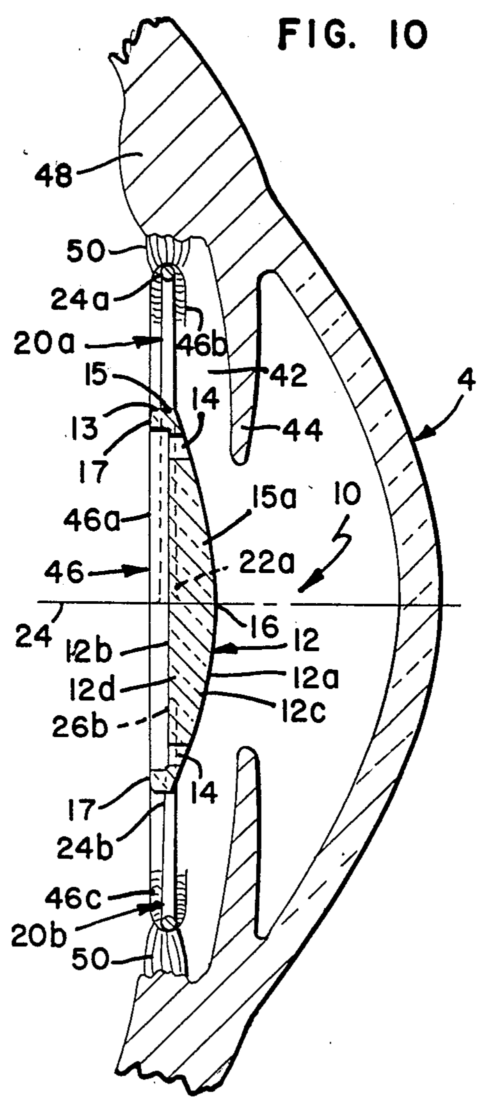
FIG. 10 is a simplified cross sectional schematic view of an eyeball with the lens of the present invention implanted in the posterior chamber.
Figure 11:
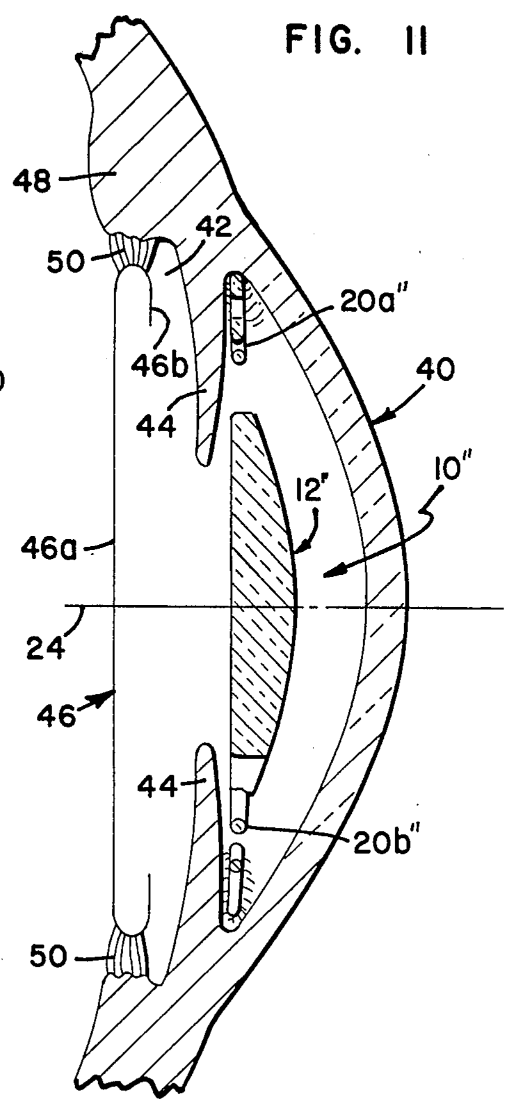
FIG. 11 is a simplified cross sectional schematic view of an eyeball implanted with the lens of the present invention implanted in the anterior chamber.

When the lens 10 is implanted in the posterior chamber of the eye, as seen in FIG. 10 the haptic elements 20*a,b* support the lens 10 by engaging the cleft or fornix portion 46*c*; thereby fixating the position of the lens 10 in the eye 40.

Figure 9:
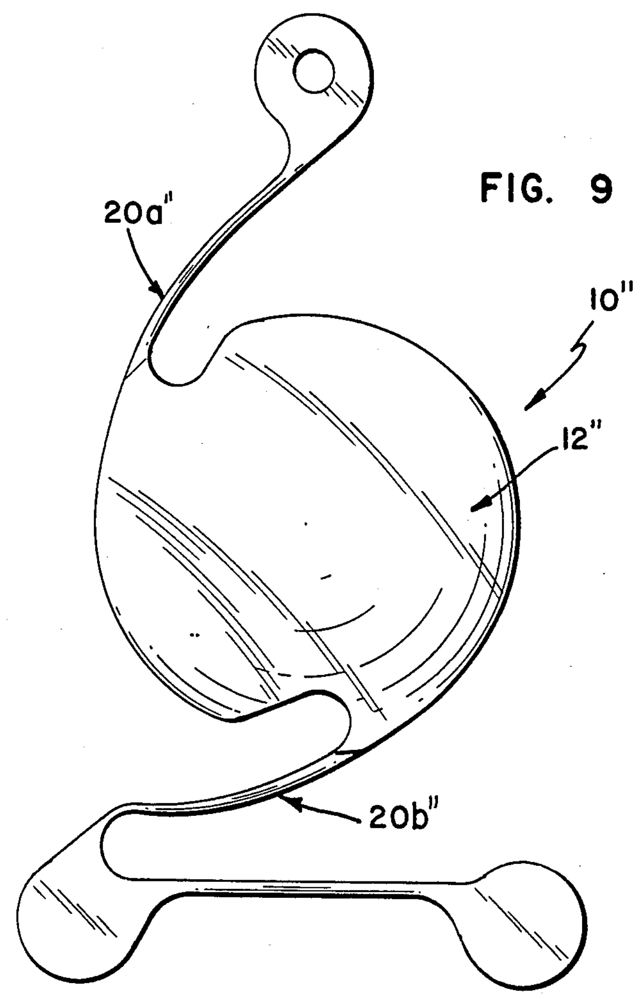
FIG. 9 is a top plan view of still another embodiment of the intraocular lens of the present invention.

When the lens 10 is adapted to be implanted in the anterior chamber of the eye 40 as seen in FIG. 11, the haptic members 20*a",b"* support the lens 10" in a spaced relationship anterior to the iris 44 of the eye 40. Specific design characteristics of a lens suitable for implanting in the anterior chamber, such as proper curvature of the haptic members 20*a",b"* and the determination of the angle at which the haptics 20*a",b"* project from the lens body 12" are known by those skilled in the art. One embodiment of an anterior chamber lens is shown in FIG. 9, and parts thereof similar to lens 10 carry similar numbers with double prime (") marks added.

While the above embodiments have been described with reference to a plano-convex lens, it is understood that the improved haptic member is also applicable to bi-convex lenses. The bi-convex lens would have a convex upper surface and convex bottom surface. The tapered haptics of the present invention could also be utilized with plano-concave lenses. Other modifications of the invention will be apparent to those skilled in the art in light of the foregoing description. This description is intended to provide specific examples of individual embodiments which clearly disclose the present invention. Accordingly, the invention is not limited to these embodiments or to the use of elements having specific configurations and shapes as presented herein. All alternative modifications and variations of the present invention which follows in the spirit and broad scope of the appended claims are included.

What is claimed:

1. An intraocular lens comprising;

(a) an optical lens body;

(b) means for positioning and supporting said lens body in an eye, including at least one resilient, fiber like haptic member having a root end connected to said lens body and a free end, said haptic member extending outwardly from said lens body with at least a portion thereof tapered along all cross sectional dimensions in a direction therealong from said root end toward said free end, said free end having a smaller cross sectional dimension than said root end.

2. An intraocular lens according to claim 1 wherein said haptic member is integrally formed with said lens body as a one-piece construction at said root end.

3. An intraocular lens according to claim 1 wherein said haptic member is tapered along all dimensions from said root end to a tip of said free end.

4. An intraocular lens according to claim 2 wherein said haptic member extends tangentially from a periphery of said lens body.

5. An intraocular lens according to claim 1 wherein said haptic member has a circular cross section.

6. An intraocular lens suitable for use as an artificial lens implant in an eye, the lens comprising:

(a) an optical lens body having a periphery;

(b) two curved elongated and resilient, fiber like haptic member for positioning and supporting said lens in the eye, said haptic members each having a root end and a free end, said haptic members being integrally formed with said lens body as a one-piece construction at said root end thereof and extending tangentially outwardly from a periphery of said lens body along an arc exterior to the periphery of said lens body, said haptic members each having at least a portion thereof tapered along all cross-sectional dimensions in a direction therealong from said root end toward said free end with said free end having a smaller cross-sectional dimension than said root end.

7. An intraocular lens according to claim 6 wherein said haptic members are positioned substantially opposite one another.

8. An intraocular lens according to claim 6 wherein said haptic members are tapered along all dimensions from said root end to a tip of said free end.

9. An intraocular lens according to claim 6 wherein each said haptic member has a circular cross section.

10. An intraocular lens suitable for use as an artificial lens implant positioned in the posterior chamber of an eye; adjacent the posterior capsule; the lens comprising;

(a) an optical lens body having a periphery, upper and bottom surfaces and a generally annular lip projecting only rearwardly from said bottom surface so as to space said lens body from the posterior capsule when said lens is positioned in the posterior chamber;

(b) two curved elongated fiber like haptic members for positioning and supporting said intraocular lens in the eye, said haptic members each having a root end and a free end including a tip, said root ends being integrally formed with said lens body to form a one-piece lens, said haptic members extending tangentially from said lens body along an arc exterior to the periphery of said lens body, said haptic members further being resilient so as to spontaneously tend to return to a normal position when released after being forced into a deformed position and having at least a portion thereof tapered along all cross-sectional dimensions in a direction therealong from said root end toward said free end with said free end having a smaller cross-sectional dimension than said root end to strengthen said haptic members.

* * * * *